United States Patent [19]

Hagedorn

[11] 4,226,114
[45] Oct. 7, 1980

[54] METHOD AND APPARATUS FOR ANALYSIS OF SUBSTANCES BY CHANGE IN ENTHALPY DURING DISSOLUTION

[75] Inventor: Fritz Hagedorn, Sehnde, Fed. Rep. of Germany

[73] Assignee: Kali-Chemie Aktiengesellschaft, Hanover, Fed. Rep. of Germany

[21] Appl. No.: 21,140

[22] Filed: Mar. 16, 1979

[30] Foreign Application Priority Data

Mar. 18, 1978 [DE] Fed. Rep. of Germany ....... 2811945

[51] Int. Cl.³ .......................................... G01N 25/48
[52] U.S. Cl. .................................. 73/61 R; 73/190 R
[58] Field of Search ..................... 73/61 R, 53, 190 R; 422/51

[56] References Cited

U.S. PATENT DOCUMENTS

| | | | |
|---|---|---|---|
| 2,891,401 | 6/1959 | Heinrich et al. | 73/190 R |
| 3,436,190 | 4/1969 | Priestley et al. | 73/190 R X |
| 3,646,812 | 3/1972 | Ishii | 73/190 R |
| 3,716,333 | 2/1973 | Peuschel et al. | 73/190 R X |
| 3,768,973 | 10/1973 | Wasilewski | 73/190 R X |
| 4,042,328 | 8/1977 | Seymour | 73/190 R X |

OTHER PUBLICATIONS

Scholl, F. Automatic Procedure for the Determination of the Lead Oxide Content of "Gray Oxides" by Measurement of the Heat of Solution. In Anal. Chem. vol. 245, p. 49–54, 1969.

Primary Examiner—Anthony V. Ciarlante
Assistant Examiner—Joseph W. Roskos
Attorney, Agent, or Firm—Schwartz, Jeffery, Schwaab, Mack, Blumenthal & Koch

[57] ABSTRACT

Disclosed is a method for the analysis of a mixture of substances comprising at least one component which dissolves with a change in enthalpy, comprising the steps of introducing a predetermined amount of the mixture of substances into a uniformly flowing stream of a solvent maintained at a constant temperature; measuring the maximum change of temperature occurring in the stream of solvent after the point of introduction; and comparing this measured maximum change in temperature with a standard measurement. Also disclosed is an apparatus for carrying out this method.

24 Claims, 8 Drawing Figures

METHOD AND APPARATUS FOR ANALYSIS OF SUBSTANCES BY CHANGE IN ENTHALPY DURING DISSOLUTION

BACKGROUND OF THE INVENTION

The invention concerns a process and apparatus for the analysis of mixtures of substances which comprise at least one component which is soluble with a change in enthalpy, whereby the changes in temperature resulting from the dissolution of said component in the solvent serve as a measure of the content of the component in the mixture of substances.

Substantial changes in enthalpy occur upon the dissolution of numerous substances. The present invention utilizes this phenomenon, which otherwise is primarily of scientific interest, for the analysis of mixtures of substances, wherein the component to be determined is present in a mixture with secondary components causing lesser changes in enthalpy during their dissolution, or are indifferent in this respect, or only slightly soluble or insoluble. The invention takes advantage of this property particularly in the analysis of mixtures wherein the component to be determined is present in high concentration. The performance of analysis of samples of this type frequently requires a laborious, time-consuming preparation of a sample solution and therefore does not lend itself to automation. Also, conventional methods of analysis, especially in production control, whereby a large number of analyses must be performed within a short period of time, are often excessively expensive, not rapid enough and pose high requirements with respect to personnel.

SUMMARY OF THE INVENTION

It is therefore an object of the invention to provide a method of routine analysis by utilizing the change in enthalpy occurring during the dissolution of substances.

Another object of the present invention is to provide such a method which makes it possible to rapidly analyze a large number of individual samples having a high content of the valuable component, with adequate accuracy and by unskilled personnel.

A specific object of the invention resides in the provision of a method for the examination of potassium fertilizer, in particular the examination of intermediate flotation products, such as those obtained in the concentration of potassium chloride and the separation of potassium chloride from sodium chloride and other undesirable contaminants.

It is also an object of the present invention to provide an apparatus for carrying out the method according to the invention.

In accomplishing the foregoing objects, there has been provided in accordance with the present invention, a method for the analysis of a mixture of substances comprising at least one component which dissolves with a change in enthalpy, comprising the steps of introducing a predetermined amount of the mixture of substances into a uniformly flowing stream of a solvent maintained at a constant temperature; measuring the maximum change of temperature occurring in the stream of solvent after the point of introduction; and comparing the measured maximum change in temperature with the maximum changes in temperature measured previously by analysis of equal amounts of similar mixtures of substances having a known content of the component. In this way the changes in temperature resulting from the dissolution of the component in the solvent serve as the measure of the content of the component in the mixture of substances.

In accordance with another aspect of the invention, there has been provided an apparatus for carrying out the above-described process of analysis, comprising: a vessel having an inlet for the solvent maintained at a constant temperature and an outlet for the solvent; means, located adjacent to the inlet, for introducing the mixture of substances into the vessel; means, located adjacent to the outlet, for measuring the temperature of the solvent; means for providing a supply of solvent maintained at a constant temperature; and means for introducing the solvent into the vessel.

Further objects, features and advantages of the present invention will become apparent from the detailed description of preferred embodiments which follows, when considered together with the attached figures of drawing.

DETAILED DESCRIPTION OF PREFERRED EMBODIMENTS

The basic method according to the invention involves introducing a definite amount of the mixture of substances in a uniformly flowing stream of the solvent maintained at a constant temperature by means of a thermostat, measuring the maximum change in temperature occurring behind the point of introduction in the direction of flow of the solvent and comparing it with the maximum changes in temperature obtained previously by analyzing identical amounts of similar mixtures of substances having a known content of the component in question.

The conditions according to the invention, such as uniformly flowing solvent maintained at a constant temperature by means of a thermostat or a definite amount of the mixture of substances, are not intended to signify extreme absolutely constant conditions, but rather conditions attainable by conventional, commercially available means. The conditions to be observed in the interest of adequate accuracy and reproducibility of the results of the analysis will become apparent in connection with the description of the embodiments to follow hereinafter. An advantage of the uniform flow of the solvent is to be found in the elimination of the introduction of definite volumes of the solvent otherwise necessary in thermometric processes, while the thermostatic control of the solvent makes reference measurements unnecessary. It is also unnecessary to determine the total amount of heat, which is normally required in the case of thermometric processes performed batchwise in Dewar vessels. It is sufficient to determine the maximum change in temperature taking place under the equilibrium conditions of the constant inflow and outflow.

It is merely necessary to ascertain that the sample being introduced will be dissolved completely or at least substantially completely with respect to the component to be determined and that the maximum change in temperature will be allowed to become established. This may be obtained by means of a suitable retention time, i.e. flow velocity of the solvent and/or the distance of the temperature measuring point from the point of introduction, or by agitation or the use of similar means promoting mixing and dissolution, respectively. Suitable sample preparation, e.g., grinding to a uniform and fine grain size, is also conducive to dissolution and mixing.

A thermometer indicating temperatures with adequate accuracy is sufficient in the simplest case for the determination of the change in temperature. It is convenient, however, to measure the temperature with a resistance thermometer or thermistor and to record it by means of a recorder.

It is advantageous for the reproducibility of the analytical results to restrict the exchange of heat with the environment, for example, by insulating the gauge length against the environment or by maintaining the solvent, by means of a thermostat, at a temperature close to room temperature. It is also advisable, prior to the analysis, to adjust the temperature of the mixture of substances to be analyzed, to the approximate temperature of the solvent and/or to room temperature.

An apparatus suitable for carrying out the process of the invention is characterized by a solution vessel with an inlet for the solvent maintained at a constant temperature by means of a thermostat and an outlet for the solvent, means adjacent to the inlet to introduce the mixture of substances, means adjacent to the outlet for measuring and recording the temperature, a supply of solvent maintained at a constant temperature by means of a thermostat, and means for supplying the solvent to the solution vessel at a uniform rate.

Optionally, means to promote the process of dissolution, such as agitators, overflow weirs or diverting weirs may also be provided in the solution vessel.

The mixture of substances to be analyzed may be introduced manually. Slight fluctuations in the time wherein the sample is being introduced into the solvent do not affect the result of the analysis. To insure the reproducibility and comparability of the results of the analysis at all times and independently of the operating personnel, a vibrating channel with a collector funnel may be provided. It is only necessary then to pour the solid sample previously weighted on a balance into the collector funnel of the vibrating channel, which in turn carries the sample into the solvent at a rate which is sufficiently constant as a function of time.

The means for measuring and recording the temperature consist of commercially available, conventional components, such as thermistors with modified Wheatstone bridge circuits with a recorder attached thereto.

A pump may be used to introduce the solvent at a uniform rate into the solution vessel from a supply of the solvent maintained at a constant temperature by means of a thermostat. This pump is connected through a conduit with the inlet of the solution vessel. Control devices, for example cocks, may be built into the conduit. The invention utilizes the pump existing in commercial thermostats, with the effective feed capacity of the pump being restricted to, for example, 500 ml/minute.

The supply of the solvent maintained at a constant temperature by means of a thermostat may consist of a thermostat filled with the solvent. The solvent is circulated through the cooling coil of said thermostat from a second source of supply maintained at a temperature lower than the temperature of the thermostat, with the volume of the solvent extracted by the pump being replaced by means of a siphon or overflow connecting the thermostat with the second source of supply. The difference in temperature between the thermostat and the second source of supply should not be excessive. Similarly, the heating input and the cooling should be correlated with each other to assure an adequate temperature constancy of the solvent.

To achieve constancy of temperature, it is advantageous to use a second thermostat filled with the solvent as the second source of supply for the firstmentioned thermostat, whereby the solvent is passed through the cooling coil of the second thermostat from a solvent supply system into a third source of supply, said third supply being maintained at a temperature lower than the temperature of the second thermostat. The volume of solvent flowing from said third supply by way of the first-mentioned siphon or overflow into the first-mentioned thermostat is replaced by means of a siphon or overflow connecting the second thermostat with the third source of supply. In this case, the difference in temperature between the second thermostat and the third source of supply may be greater. For example, if the solvent is water, the third source of supply may consist of an overflow vessel and be supplied directly from the water line via the cooling coil of the second thermostat.

Even though fluctuations of the ambient temperature do not affect the result of the analysis, but merely act to displace the base line to be described hereinafter, i.e. the zero point, it is advantageous to insulate the solution vessel, the thermostats and the overflow vessel against the environment.

A solution vessel 1 may be seen in the drawings. It is made of stainless steel and is divided by an overflow weir 2 into two chambers of equal size. An agitator 3 is immersed in each of the chambers. The solution vessel 1 has an inlet 4 for the thermostatically controlled solvent, for example water, flowing in a uniform stream in the direction of the arrows, and an outlet 5. The outlet 5 and the upper edge of the overflow weir 2 determine the water level in the solution vessel 1. They are both arranged at the same level. The useable capacity of the solution vessel is one liter. A diverting weir 6 is arranged in front (in the direction of the flow) of both the overflow weir 2 and the outlet 5. These diverting weirs extend above the surface of the water on the one hand, and close to the bottom of the solution vessel 1, on the other. The water flows under these weirs and provides, together with the agitators 3, a thorough mixing of the contents of the solution vessel. Adjacent to the inlet 4, the point of introduction, designated by reference numeral 7, of the mixture of substances to be examined is found; arranged next to the outlet 5 is a thermistor 8 for measuring and indicating the temperature. A recording instrument registers the variation in temperature. A closable opening 11 is provided in each chamber of the solution vessel 1, whereby insoluble components potentially present in the mixture of substances to be analyzed may be flushed out. The solution vessel is insulated on all sides against the environment. An existing cover with openings for the agitators 3, for the thermistor 8 and for the introduction of the mixture of substances is not shown in FIG. 1, but is illustrated in FIGS. 2 and 3. In FIG. 2 and (rotated by 90°) in FIG. 3, a vibrating channel 12 with a collector funnel 13 is additionally illustrated, while here the measuring and indicating instrument 9 and the recorder 10 are omitted.

In order to maintain a uniform flow of constantly thermostatically controlled water, two thermostats, designated overall with the reference numbers 14 and 15, and an overflow vessel 16, are provided. By the term "thermostat" is meant a thermostatically controlled heating and/or cooling vessel. The heating and control devices of the thermostats and the installations for the circulation and mixing, respectively, of the water within the termostats, are not shown. They are conventional. A pump 17 is immersed in the water supply of the first thermostat 14 (viewed counter to the direction of flow from the solution vessel) said pump 17 feeding via conduit 18 and the inlet 4 into the solution vessel 1. Control devices, for example cocks and the like, not shown, may be built into the conduit 18. The pump 17 is a pump installed in commercially available thermostats, and in the case of a useable capacity of the solution vessel of 1 liter, as chosen for illustration herein, has an effective feed capacity of 500 ml/minute, controlled by means of cocks (not shown) in the conduit 18. The temperature set for the first thermostat 14 is not particularly critical. It is selected preferably at approximately room temperature to minimize the exchange of heat with the environment. The cooling coil 19 of the first thermostat 14 is connected with a pump 21 immersed in the water supply of the second thermostat 15 (viewed counter to the direction of flow from the solution vessel) by means of a conduit 20, said pump feeding back into the thermostat 15 via a return line 22. The temperature of the second thermostat 15 is set slightly, for example, about 1.5° C., under the temperature of the first thermostat. This very careful cooling, together with a corresponding low heat input in the first thermostat 14, results in the fact that the temperature fluctuations of the water freely flowing (i.e., without the effect of the possible addition of a sample) at the point of measurement are less than ±0.015° C. The water moved by the pump 17 from the first thermostat 14 into the solution vessel 1, is replaced by means of a siphon and a connecting line 23, respectively, from the water supply of the second thermostat 15.

The cooling coil 24 of the second thermostat 15 is connected by means of a conduit with a water faucet 26 of a water supply system, for example, the public water supply system. The cooling water flows through a conduit 27 into the overflow vessel 16 and from there to a drain, by means of the overflow 28. The water flowing from the second thermostat 15 into the first thermostat 14 is replaced by means of a siphon and a connecting line 29, respectively, from the overflow vessel 16. It should be understood that the flow from the water faucet 26 into the overflow vessel 16 must not be less than the effective feed rate of the pump 17 in the first thermostat, because the thermostats 14, 15 and the overflow vessel 16 would otherwise run dry.

Figure 1:
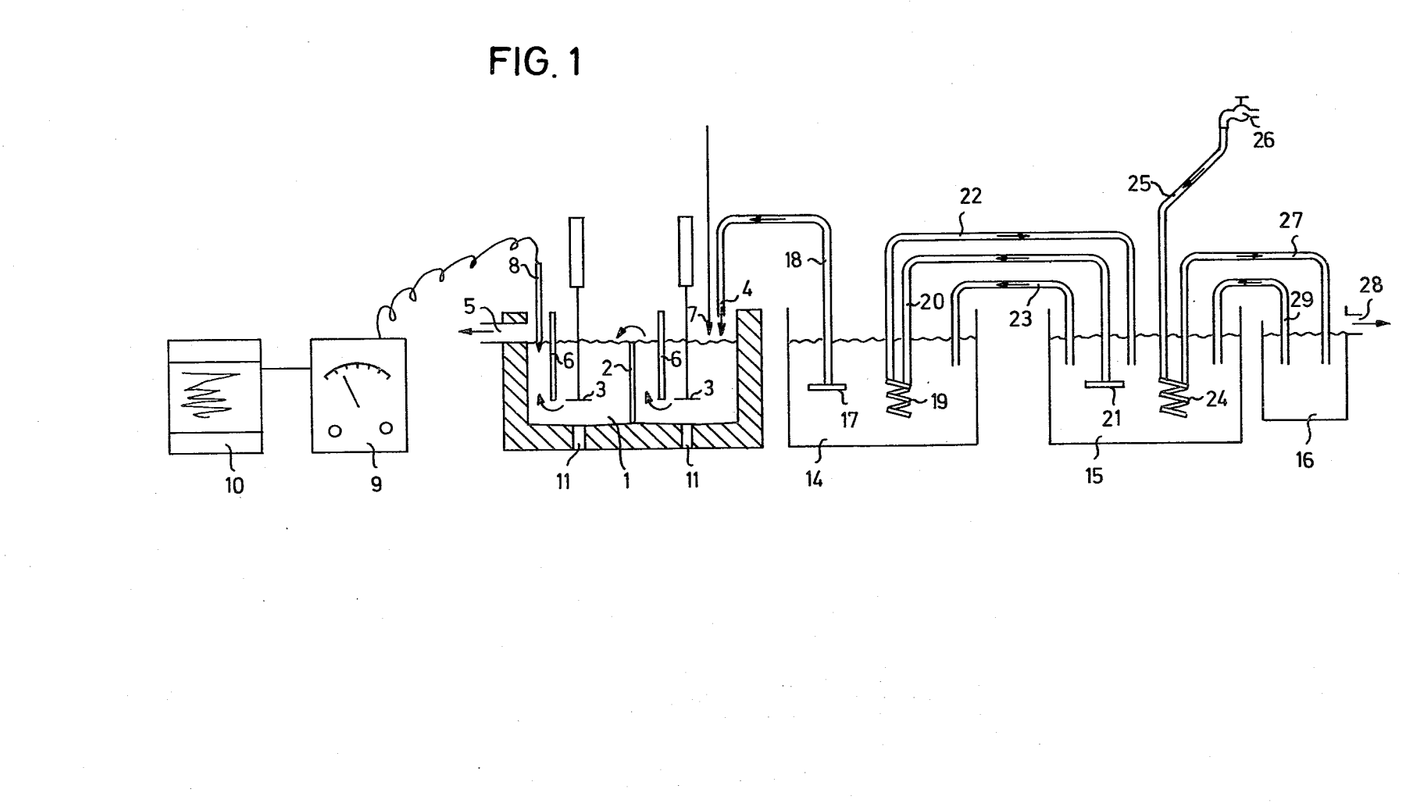
FIG. 1 is a schematic view of an apparatus according to the present invention.
Figure 2:
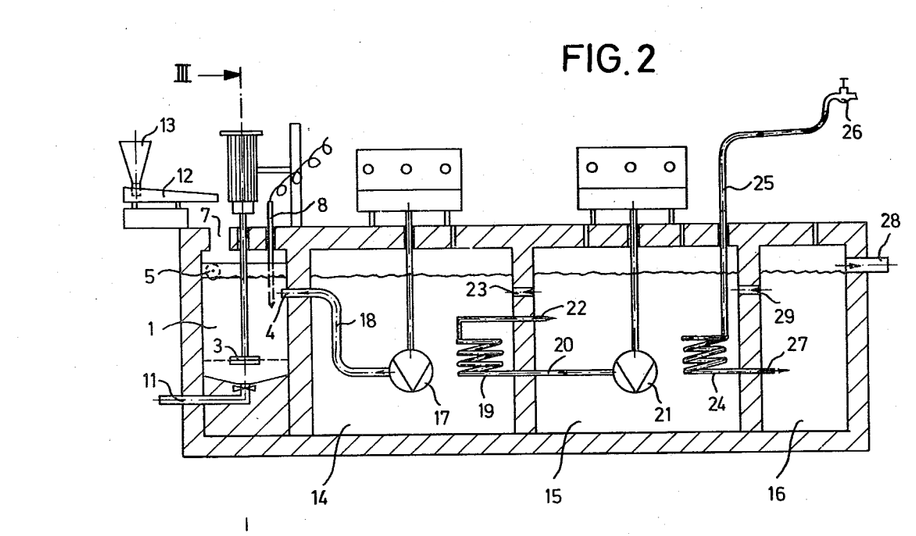
FIG. 2 is a schematic of a front elevation view of an analytical apparatus, which has been adapted specifically to the process of the invention.
Figure 3:
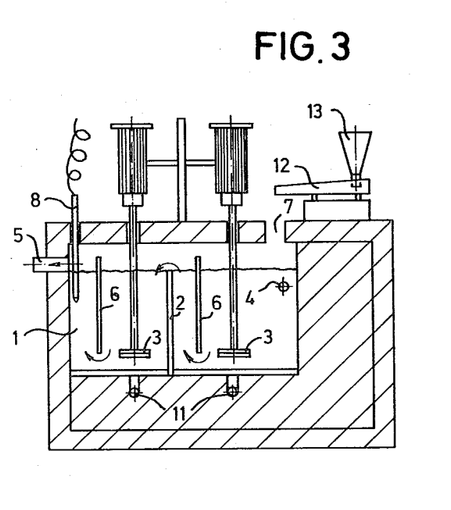
FIG. 3 is a sectional view taken along the line III—III in FIG. 2.

The embodiment of FIGS. 2 and 3 differs from that of FIG. 1 essentially in that the thermostats and the overflow vessel are combined in a single block and insulated on all sides. Similarly, all of the abovementioned connecting lines are placed within the insulation.

The mode of operation of the apparatus is as follows: As soon as the preselected temperatures in the thermostats are attained, subsequent to opening of the water faucet 26, actuation of the pumps 21, 17, the agitators 3, and the heaters in the thermostats, and after the system has established its state of equilibrium, indicated by the fact that the recorder of the temperature measuring system is drawing a constant line, i.e., the base line, the weighed solid sample, for example 100 g, is introduced at the point 7 into the front chamber of the solution vessel 1, either manually or by means of the funnel 13 and the vibrating channel 12.

Figure 5:
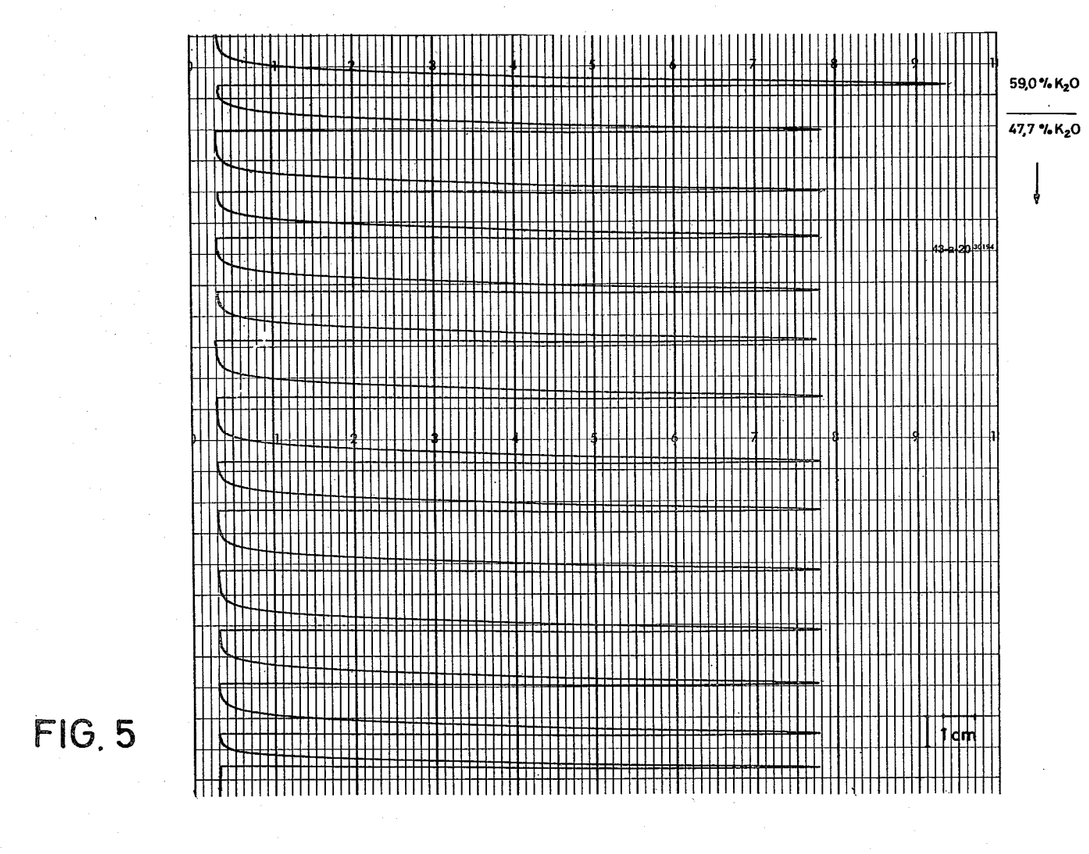

Under the effect of the agitator 3, the diverting weir 6 and the overflow weir 2, the sample is rapidly dissolved and the contents of the solution vessel are intermixed. The increase or decrease of the temperature of the water occurring as the result of the dissolution is measured in the vicinity of the outlet 5 by means of the thermistor 8 and is registered by the recorder 10. The recorder registers a peak, with the height thereof above the base line, corresponding to the variation of the water temperature. Repetition of the process several times using the same amount of the same substance yields a recorder diagram as shown in FIG. 5. It is merely necessary to insure that subsequent samples do not affect each other, which may be ascertained most simply by observing the return of the recording pen to the base line corresponding to the temperature of the thermostatically controlled solvent.

Figure 4:
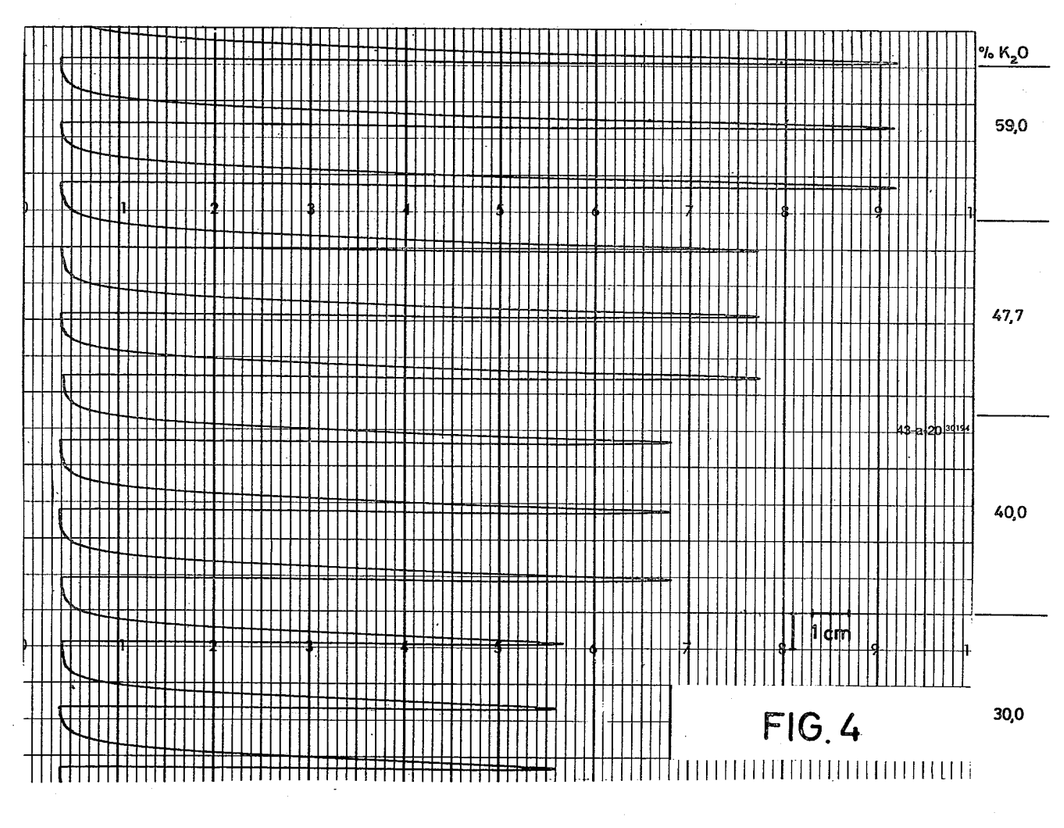
FIGS. 4 through 8 are recorder diagrams from the process of the present invention.

The repetition of the process with identical amounts of the sample, but with said samples containing different, controlled amounts of the component to be determined, as ascertained previously by other means, results in a calibrating diagram, such as the one shown in FIG. 4. With the aid of such a calibrating diagram, a calibrating curve may be established. The calibrating curve has a zero point located in actual operation on the base line, together with a scale graduated, for example, in percents, so that, if the scale is correlated with the peak value, the content of the component to be determined may be read from it. It is merely necessary to insure that identical amounts of the sample, e.g., the above-mentioned 100 g, are always measured into the solution vessel and that the individual calibrating samples are extensively identical in their composition with the samples to be analyzed in order to eliminate the effect of secondary components. In the case of the large weighed sample of 100 g, large erros in weighting may be acceptable. Weighing on a top pan scale is sufficient. As may be seen from the examples of applications to be presented hereinafter, with the conditions selected herein (sample weight 100 g, effective discharge capacity of the pump 17, 500 ml/minute, useable capacity of the solution vessel 1 liter), the deviation range of the analytical results is better than ±0.5% absolute, with a probability of overshooting of 5%. This is adequate for the basic applications of the invention.

The state of equilibrium of the system is reestablished as a rule in 2 to 3 minutes following the introduction of the sample, so that a sequence of at least 10 samples per hour may be realized. (The diagrams of FIG. 4 to 8 were written with a paper feed rate of 30 cm/minute; the diagrams of FIG. 4 and 6 to 8 have been slightly reduced in size, the diagram of FIG. 5 has been a little more reduced in size(*)). Fluctuations in the length of the addition period, within reasonable limits, e.g. between 15 and 37 seconds, do not affect the results of the analysis. Even though a change in the room temperature in the case of an inadequate insulation of the apparatus leads to a drift in the base line, the height of the peak is not affected, so that if a standard curve is available, the result of the analysis remains the same. Differences in the range of grain sizes again have no effect, provided that a certain grain size is not exceeded, whereby said grain size is a function of the nature and the solubility of the sample.

(*) than those of FIG. 4 and 6 to 8; in any case, the original length of 1 cm is shown on the diagrams graphically.

The following examples are presented to illustrate the use of the invention, without in any way limiting the invention.

EXAMPLE 1

Determination of the $K_2O$ Content of Potassium Fertilizer Salts and Intermediate Manufacturing Products The dissolution of potassium chloride in water is accompanied by an appreciable cooling effect, while sodium chloride, which is dissolved as a secondary component, causes only a slight change in enthalpy.

A sample of 100 g of the salt to be analyzed is weighed out and introduced by means of a vibrating channel into the front chamber of the solution vessel.

Calibration is effected by means of natural salts, whereby the different $K_2O$ content of these salts is determined by repeated analysis using conventional methods. A calibration diagram, such as the one represented in FIG. 4, is obtained. With the aid of the peak heights, a calibrating curve is constructed and a calibrating ruler produced, which may be used in the evaluation.

The deviation range (random error), with an overshoot probability of 5%, amounts to $\pm 0.36\%$ $K_2O$. This value was determined by means of 13 consecutive analyses of a fertilizer salt with 47.7% $K_2O$. (FIG. 5).

If the temperature of the salt differs by $\pm 2.0°$ C. from the temperature of the flowing water, this results in an increase in the deviation range to $\pm 0.47\%$ $K_2O$.

An increase in the room temperature by 12° C. leads to a drift, when the experimental apparatus of FIG. 1 is used, but it does not affect the height of the peaks, so that if an evaluating scale is used, there is no change in the analytical results.

Similarly, introduction periods of varying lengths (15 and 37 seconds) and different grain size ranges—provided that the material has been ground to a grain size less than about 0.5 mm—have no effect on the results of the analysis.

EXAMPLE 2

Determination of the Sodium Bicarbonate Content in Anhydrous Soda

In the case of incorrect storage of anhydrous soda, re-forming of sodium bicarbonate may take place due to the effect of water and carbon dioxide from the air. Constant surveillance of the product, both by the producer and the consumer, is thus necessary. The above-described process makes it possible to determine the sodium bicarbonate content very simply and rapidly.

For the analysis, 100 g of the sample to be examined are weighed out and introduced into the solution vessel by means of a vibrating channel. The result is available in 2 minutes. This includes the time required for the weighing of the sample.

Figure 6:
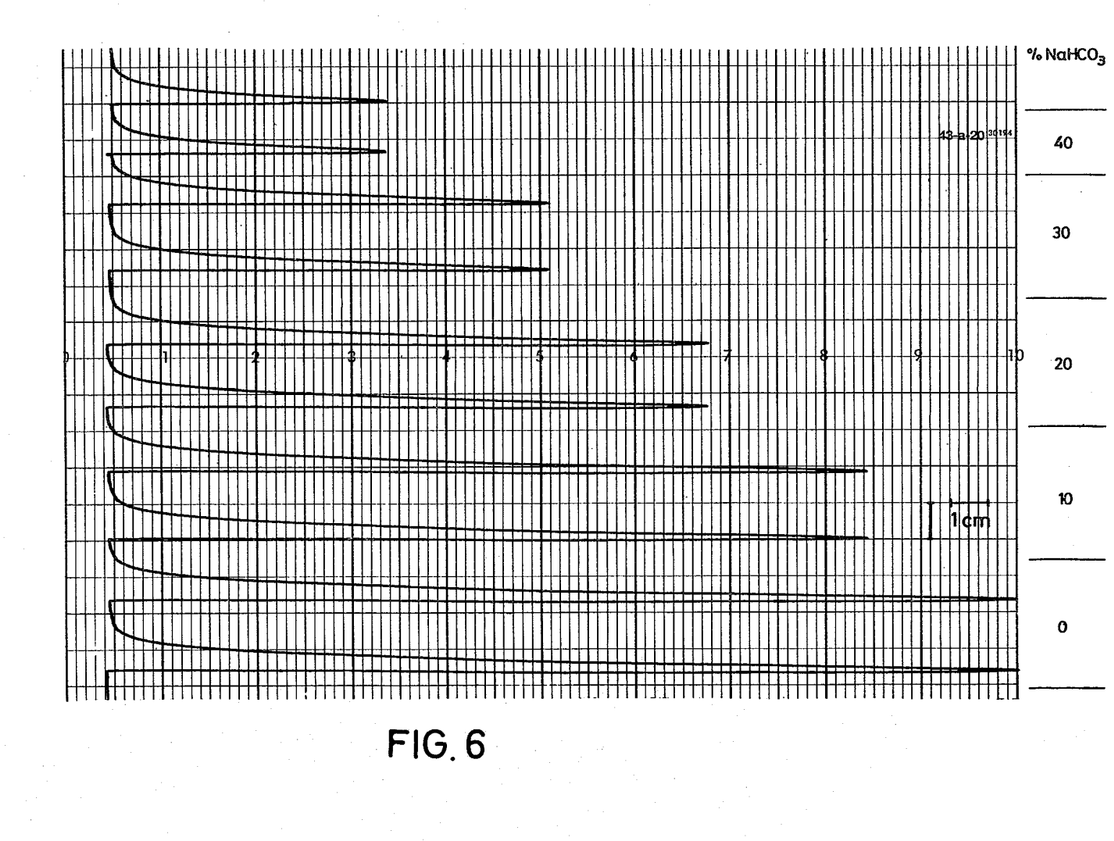
Figure 7:
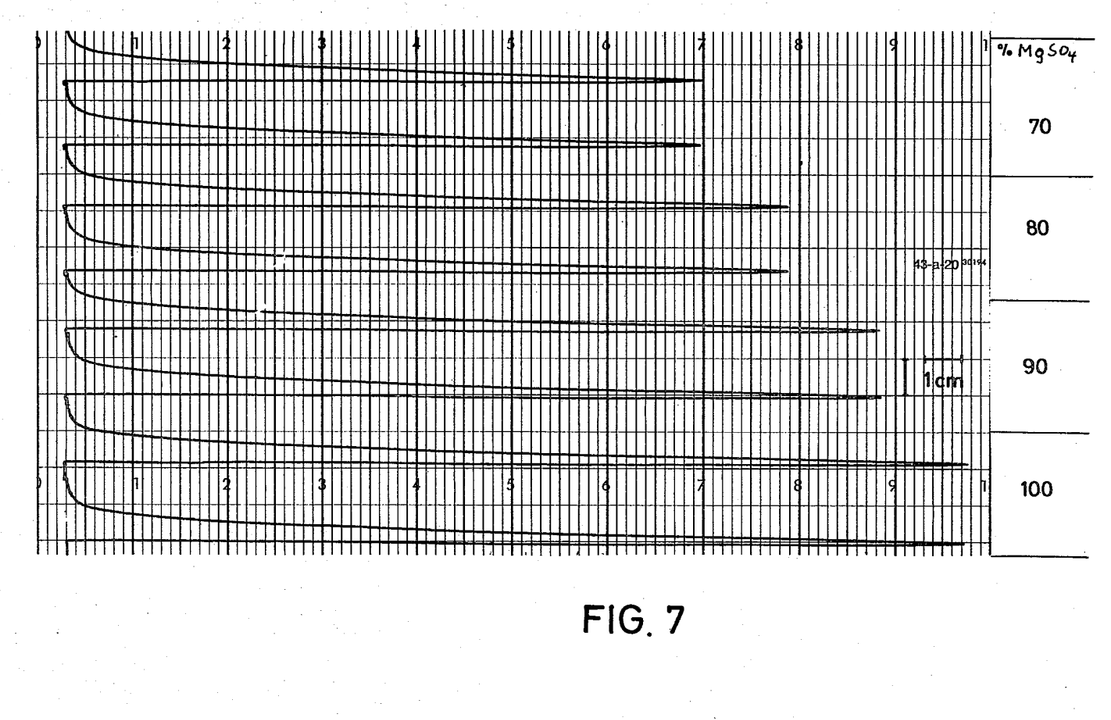
Figure 8:
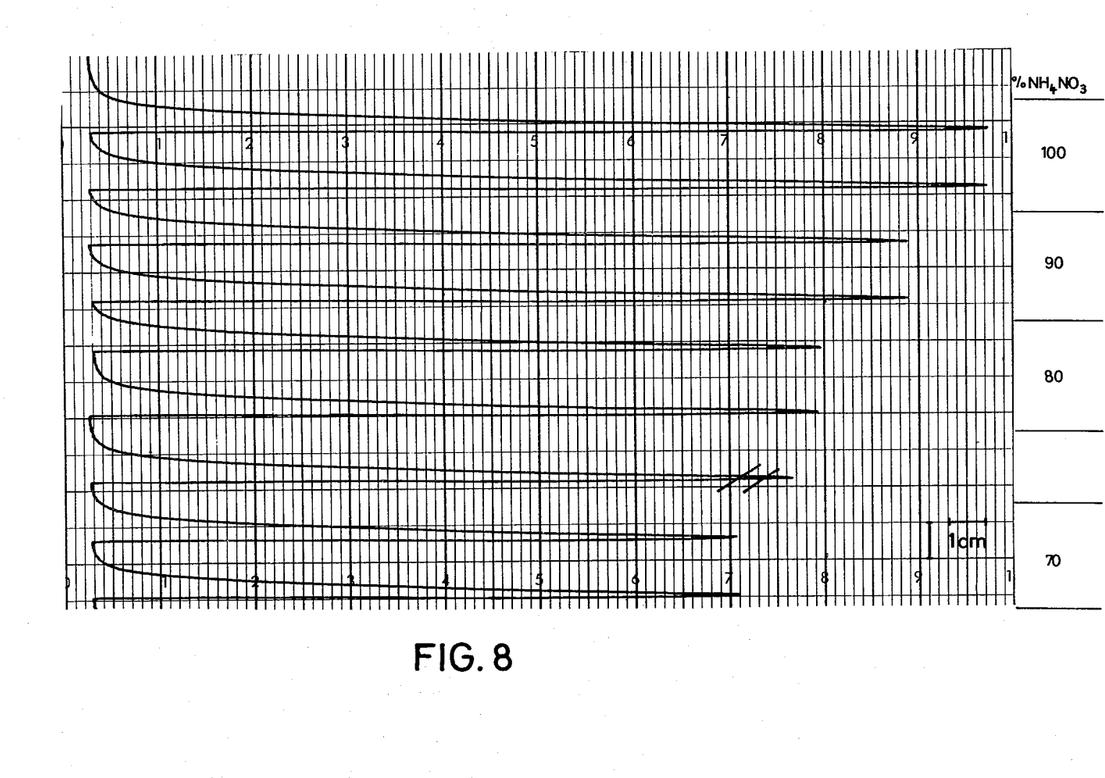

Calibration is effected by means of the introduction of synthetic mixtures of anhydrous sodium carbonate and sodium bicarbonate. The resulting calibration diagram is shown in FIG. 6.

An evaluating ruler is prepared with the aid of this diagram. The deviation range amounts to $\pm 0.15\%$ $Na_2CO_3$, with an overshoot probability of 5%.

EXAMPLE 3

Surveillance of a Calcining Process

In various potassium works, in addition to potassium chloride, kieserite ($MgSO_4.H_2O$) is also produced. This mineral dissolves very slowly in cold water. Dehydration may become necessary during processing, to accelerate the solution process. The control of the calcining process, for the purpose of regulating the flow rate, the retention time and the temperature, requires numerous relatively time-consuming investigations. With the aid of the above-described process, such controls may be effected very rapidly and simply.

For the analysis, 100 g. of the sample to be analyzed are weighed and introduced by means of a vibrating channel into the solution vessel. One minute later the result may be read from the recorder.

Calibration is effected by means of the introduction of completely dehydrated kieserite and mixtures of this substance with various proportions of the nondehydrated material. The result is a calibrating diagram such as the one shown in FIG. 7.

EXAMPLE 4

Determination of Ammonium Nitrate in Explosives

Explosives used primarily in mining contain, in addition to ammonium nitrate, an organic component. The ammonium nitrate content is between 90 and 100% and must be determined frequently in production control. Analysis in these concentration ranges is rather difficult.

With the aid of the above-described process, such analysis may be performed very simply and rapidly.

A sample of 100 g. of the explosive to be examined is weighed out and introduced into the solution vessel by means of a vibrating channel. One minute later the result of the analysis is available.

Calibration is effected by means of the introduction of samples with a known proportion of the organic substance. The result is a calibrating diagram such as the one presented in FIG. 8. By means of dual determinations, a deviation range of $\pm 0.4\%$ $NH_4NO_3$ was determined (overshoot probability: 5%).

The advantages of the invention may be summarized as follows:

1. The invention is particularly suitable for routine analysis to control processes within a production plant installation.

2. Because of the simple handling required (the weighing of a relatively large sample quantity and introduction into the funnel of a vibrating channel), the analysis may be performed by unskilled operating personnel.

3. Complete automation of the process is possible with the use of suitable metering devices (e.g. automatic scales).

4. In the presence of insoluble components in the mixture of substances, the insoluble component may be flushed out between two individual samples by opening (manual or automatic) for a short period of time the bottom valves of the chambers of the solution vessel.

Rinsing is accomplished by means of the constantly flowing stream of water.

5. In place of water, another not overly expensive solvent, for example, a dilute acid or an organic solvent, may be used. This fact considerably broadens the application range of the invention. In the case of a dilute acid, an acid of a higher concentration will be metered into an additional prechamber of the solution vessel with agitation.

What is claimed is:

1. A method for the analysis of a mixture of solid substances comprising at least one soluble component which dissolves with a change in enthalpy, comprising the steps of introducing at a first point a predetermined amount of the mixture of substances in solid form into a uniformly flowing stream of a solvent for the soluble component maintained at a constant temperature; measuring the maximum change of temperature occurring in the stream of solvent at a second point in the stream downstream of the first point of introduction; and comparing said measured maximum change in temperature with the maximum changes in temperature measured previously by analysis of equal amounts of similar mixtures of substances having a known content of said component, whereby the changes in temperature resulting from the solution of said component in the solvent serve as the measure of the content of said component in said mixture of substances.

2. A method according to claim 1, wherein said second point where said measuring step is carried out comprises a point where the component to be determined is completely dissolved in said solvent.

3. A method according to claim 2, further comprising agitating the solvent subsequent to said introducing step, whereby dissolution of the mixture of substances is promoted.

4. A method according to claim 3, further comprising the step of treating the mixture of substances prior to said introducing step to place it into a condition facilitating dissolution.

5. A method according to claim 4, wherein said temperature measurement is carried out by means of a resistance thermometer and further comprising the step of recording the variation in temperature.

6. A method according to claim 5, further comprising minimizing the exchange of heat between said flowing stream and the environment.

7. A method according to claim 6, wherein the solvent is maintained at a temperature close to the ambient temperature.

8. A method according to claim 7, wherein the mixture of substances is adjusted to the approximate temperature of the solvent prior to said introducing step.

9. A method of analysis according to claim 1, wherein said mixture of substances comprises potassium fertilizer salts and said component comprises potassium.

10. A method of analysis according to claim 1, wherein said mixture of substances comprises anhydrous soda and said substance comprises sodium bicarbonate.

11. A method of analysis according to claim 1, wherein said mixture of substances comprises hydrous and anhydrous kieserite and said substance comprises anhydrous kieserite.

12. A method of analysis according to claim 1, wherein said mixture of substances comprises an explosive and said substance comprises ammonium nitrate.

13. A method of analysis according to claim 1, further comprising the steps of maintaining an amount of said solvent in a supply container at a predetermined constant temperature and continuously withdrawing a portion of solvent from said supply container to provide said stream of solvent at a constant temperature.

14. An apparatus for carrying out a process of analyzing a mixture of solid substances including at least one soluble component which dissolves with a change in enthalpy, comprising:
means for providing a supply of a solvent for the soluble component maintained at a predetermined constant temperature;
a vessel having an inlet for the solvent maintained at a constant temperature and an outlet for said solvent;
means for continuously withdrawing a portion of the solvent from said providing means and introducing the withdrawn solvent into said vessel inlet to produce a uniformly flowing stream of said solvent through said vessel between its inlet and its outlet;
means, located adjacent to said inlet, for introducing the mixture of solid substances into said stream of solvent as it enters said vessel; and
means, located adjacent to the outlet, for measuring the temperature of said stream of solvent as it exits from said vessel.

15. An apparatus according to claim 14, further comprising means for promoting dissolution of the mixture of substances in the vessel.

16. An apparatus according to claim 15, wherein said dissolution promoting means comprises at least one agitator in said vessel.

17. An apparatus according to claim 15, wherein said dissolution promoting means comprises at least one weir in said vessel for diverting the flow of said solvent.

18. An apparatus according to claim 16 or 17, wherein said means for introducing said mixture of substances comprises a vibrating channel having a collector funnel associated therewith.

19. An apparatus according to claim 18, wherein said temperature measuring means comprises a thermistor and further comprises means for recording the temperature.

20. An apparatus according to claim 19, wherein the means for withdrawing the solvent from said providing means and introducing the solvent into the vessel comprises a pump feeding from the supply of solvent through a conduit directed to said vessel.

21. An apparatus according to claim 20, wherein said means for providing a supply of solvent maintained at a constant temperature comprises a thermostat containing said solvent, a second supply of said solvent maintained at a temperature lower than that of said thermostat, a cooling coil in said thermostat, means for circulating said solvent from said second supply through said cooling coil and back to said second supply, and a siphon or overflow connecting the thermostat with the second solvent supply whereby the quantity of the solvent removed by said pump is replaced by said siphon or overflow.

22. An apparatus according to claim 21, wherein said second solvent supply comprises a second thermostat having a cooling coil therein and being filled with the solvent, and said apparatus further comprises a third solvent supply, means for introducing solvent from a solvent supply system through the cooling coil of said second thermostat into said third solvent supply, means for maintaining said third solvent supply at a temperature lower than the temperature of the second thermostat, and a siphon or overflow connecting the second thermostat with the third supply for replenishing solvent removed from said second thermostat.

23. An apparatus according to claim 22, wherein the third supply comprises an overflow vessel with any excess of the solvent in the overflow vessel being drained by means of an overflow therein.

24. An apparatus according to claim 23, wherein the vessel, the first and second thermostats and the overflow vessel include means for insulating them against the environment.

* * * * *